US 8,237,783 B2
Aug. 7, 2012

(12) United States Patent
Yamazaki

(54) IMAGE PROCESSING DEVICE FOR ENDOSCOPE AND ENDOSCOPE APPARATUS

(75) Inventor: Kenji Yamazaki, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 782 days.

(21) Appl. No.: 12/266,280

(22) Filed: Nov. 6, 2008

(65) Prior Publication Data
US 2009/0066787 A1 Mar. 12, 2009

Related U.S. Application Data

(63) Continuation of application No. PCT/JP2007/058859, filed on Apr. 24, 2007.

(30) Foreign Application Priority Data

May 8, 2006 (JP) .................................. 2006-129681

(51) Int. Cl.
*H04N 7/18* (2006.01)
*A62B 1/04* (2006.01)
(52) U.S. Cl. ............................................ 348/70; 348/65
(58) Field of Classification Search .................... 348/65, 348/68; 600/109, 180
See application file for complete search history.

(56) References Cited

U.S. PATENT DOCUMENTS

| 5,187,572 A | 2/1993 | Nakamura et al. |
| 5,408,263 A * | 4/1995 | Kikuchi et al. ................ 348/68 |
| 5,646,680 A | 7/1997 | Yajima |
| 2005/0020879 A1 | 1/2005 | Suzuki |
| 2007/0223797 A1 * | 9/2007 | Kaneko ........................... 348/65 |
| 2009/0118578 A1 * | 5/2009 | Takasugi et al. .............. 600/109 |
| 2009/0156901 A1 * | 6/2009 | Gono ............................. 600/180 |
| 2009/0303316 A1 * | 12/2009 | Iwasaki et al. ................. 348/65 |

FOREIGN PATENT DOCUMENTS

| CN | 1658787 A | 8/2005 |
| EP | 1 491 132 A1 | 12/2004 |
| EP | 1 527 729 A1 | 5/2005 |
| JP | 05-084218 | 4/1993 |
| JP | 2003-037775 | 2/2003 |
| JP | 2003-093336 | 4/2003 |
| JP | 2004-000335 | 1/2004 |
| JP | 3540567 | 4/2004 |
| JP | 2006-061620 | 3/2006 |
| WO | WO 2006/025334 A1 | 3/2006 |

OTHER PUBLICATIONS

English-language abstract only of Japanese Patent Application Publication No. 11-113012 dated Apr. 23, 1999.
Chinese Office Action dated Mar. 1, 2010.
Extended Supplementary European Search Report dated Apr. 23, 2010.

* cited by examiner

*Primary Examiner* — Quang N. Nguyen
(74) *Attorney, Agent, or Firm* — Scully, Scott, Murphy & Presser, P.C.

(57) ABSTRACT

An image processing device for an endoscope includes an image processing section which performs signal processing for generating an image signal to be observed as an endoscope image, for a signal picked up with an image pickup device equipped in the endoscope, a tone correcting circuit section which corrects a tone for the image signal, and a switching section which switches an observation mode or a type for observing as an endoscope image, and changes a correction characteristic of a tone by the tone correcting circuit section in accordance with switching of the observation mode or the type.

19 Claims, 9 Drawing Sheets

IMAGE PROCESSING DEVICE FOR ENDOSCOPE AND ENDOSCOPE APPARATUS

CROSS REFERENCE TO RELATED APPLICATION

This application is a continuation application of PCT/JP2007/058859 filed on Apr. 24, 2007 and claims benefit of Japanese Application No. 2006-129681 filed in Japan on May 8, 2006, the entire contents of which are incorporated herein by this reference.

BACKGROUND OF INVENTION

1. Field of the Invention

The present invention relates to an image processing device for an endoscope and an endoscope apparatus which perform change of a tone characteristic in accordance with a type or an observation mode of an endoscope image, or an emphasis level for emphasizing sharpness of the endoscope image.

2. Description of the Related Art

An endoscope apparatus is equipped in the function of emphasizing the sharpness of an endoscope image (for example, structure emphasis), and as disclosed in, for example, Japanese Patent Application Laid-Open Publication No. 2004-000335 as the first prior example, switching of an emphasis amount in accordance with an emphasis level is possible by operation of a switch or the like included in the endoscope. Thus, the endoscope images differing in sharpness can be output onto the display device. Further, an endoscope apparatus including special light observation in addition to ordinary light observation, that is, capable of observation with endoscope images of different types by switching the observation mode has also been conceived.

Further, as the method of reducing noise in the low intensity portion of an image, there is, for example, Japanese Patent No. 3540567 as the second prior example applied to an electronic camera. In the second prior art, reduction of noise is realized by specially providing a tone correction circuit for sharpness emphasis processing, which differs in a tone characteristic from that for a main signal.

SUMMARY OF THE INVENTION

An image processing device for an endoscope according to one embodiment of the present invention includes an image processing section which performs signal processing for generating an image signal which is to be observed as an endoscope image and corresponds to the endoscope image, for a signal of an image picked up with an image pickup device equipped in an endoscope, a tone correcting circuit section which corrects a tone for the image signal, and a switching section which switches an observation mode or a type for observing as an endoscope image, and changes a correction characteristic of a tone by the tone correcting circuit section in accordance with switching of the observation mode or the type.

An image processing device for an endoscope according to one embodiment of the present invention includes an image processing section which performs signal processing for generating an image signal which is to be observed as an endoscope image and corresponds to the endoscope image, for a signal of an image picked up with an image pickup device equipped in an endoscope, a tone correcting circuit section which corrects a tone for the image signal, an emphasis circuit section which performs emphasis of sharpness for the image signal, a switching section which switches an observation mode or a type for observing as an endoscope image, and an emphasis amount switching section which performs switching of an emphasis amount of the sharpness, and changes a correction characteristic of a tone by the tone correcting circuit section in accordance with at least one switching of switching of the observation mode or the type, and switching of the emphasis amount.

An endoscope apparatus according to one embodiment of the present invention includes a light source section which generates illumination light which is irradiated to a specimen and includes at least ordinary illumination light of a visible wavelength region, an endoscope including an image pickup section picking up an image of the specimen in return light from the specimen, an image processing section which generates an image signal corresponding to an endoscope image to be observed with a display device based on a signal of an image picked up by the image pickup section, a tone correcting circuit section which corrects a tone for the image signal, and a switching section which switches an observation mode or a type for observing as the endoscope image, and changes a tone correction characteristic in the tone correcting circuit section in accordance with switching of the observation mode or the type.

An endoscope apparatus according to one embodiment of the present invention includes a light source section which generates illumination light which is irradiated to a specimen and includes at least ordinary illumination light of a visible wavelength region, an endoscope including an image pickup section picking up an image of the specimen in return light from the specimen, an image processing section which generates an image signal corresponding to an endoscope image to be observed with a display device based on a signal of an image picked up by the image pickup section, a tone correcting circuit section which corrects a tone for the image signal, a switching section which switches an observation mode or a type for observing as the endoscope image, and an emphasis circuit section which enables switching of an emphasis amount, and performs emphasis of sharpness for the image signal, and changes a tone correction characteristic in the tone correcting circuit section in accordance with at least one of switching of the mode or the type, and switching of the emphasis amount.

DETAILED DESCRIPTION OF THE PREFERRED EMBODIMENT(S)

Hereinafter, embodiments of the present invention will be described with reference to the drawings.

(Embodiment) 1

Embodiment 1 of the present invention will be described with reference to FIGS. 1 to 10.

Figure 1:
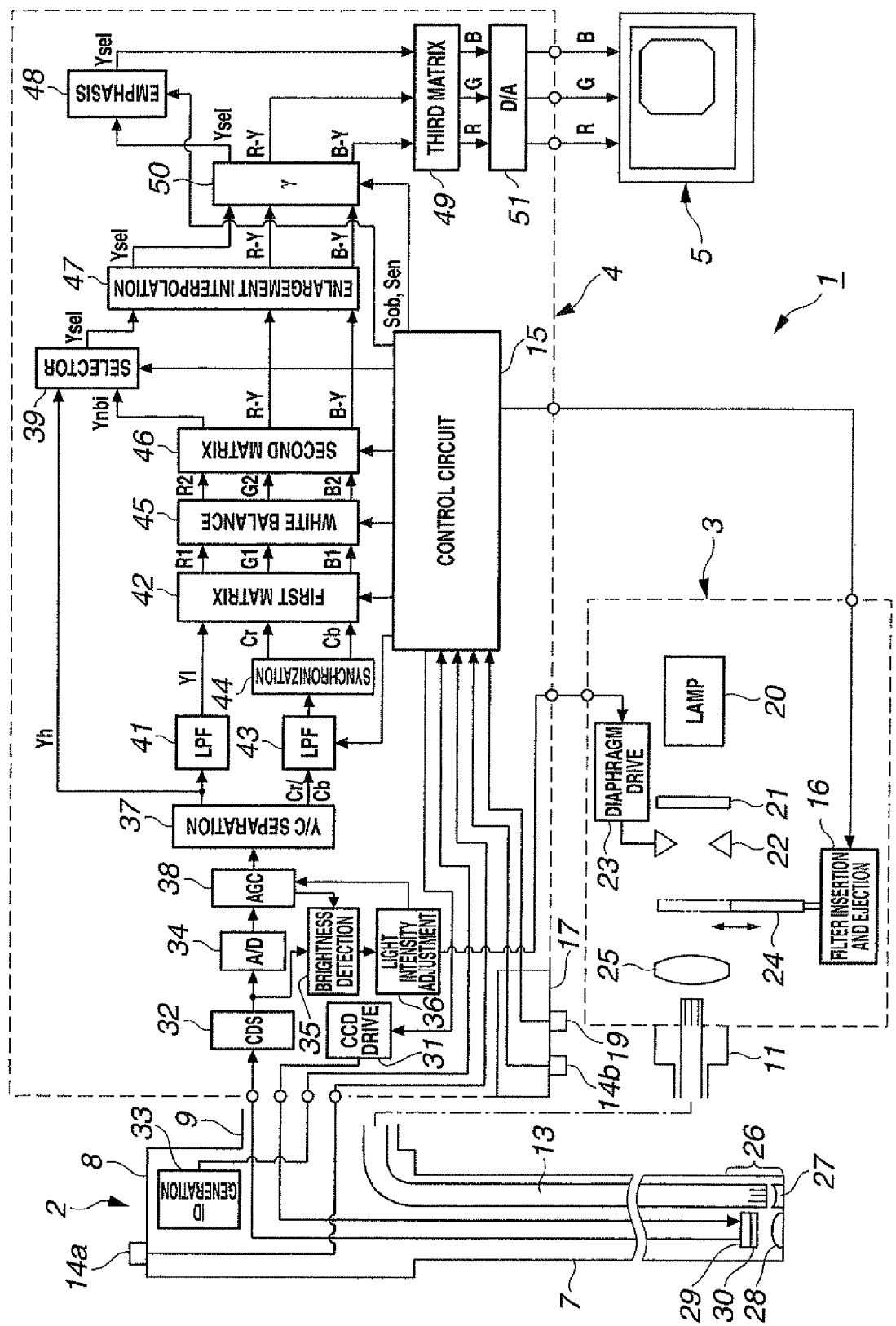
FIG. 1 is a block diagram showing an entire configuration of an endoscope apparatus including embodiment 1 of the present invention.

As shown in FIG. 1, an endoscope apparatus 1 including embodiment 1 of the present invention includes an electronic endoscope (hereinafter, simply abbreviated as an endoscope) 2 which is inserted into a body cavity or the like and performs endoscopy, a light source device 3 which supplies illumination light to the endoscope 2, a video processor 4 as an image processing device for an endoscope of embodiment 1 which drives image pickup means equipped in the endoscope 2, and performs signal processing for an output signal of the image pickup means, and a monitor 5 which displays an image signal as a corresponding endoscope image as a result that the image signal (or a video signal) output from the video processor 4 is input into the monitor 5.

The endoscope 2 has an elongated insertion portion 7, an operation portion 8 provided at a rear end of the insertion portion 7, and a universal cable 9 which is extended from the operation portion 8. A light guide connector 11 at an end portion of the universal cable 9 is detachably connected to the light source device 3, and a signal connector is detachably connected to the video processor 4.

A light guide 13 which transmits illumination light is inserted into the above described insertion portion 7. The light guide connector 11 at an end portion on a hand grip side in the light guide 13 is connected to the light source device 3, and thereby, the illumination light of the light source device 3 is supplied to the light guide 13.

The light source device 3 generates illumination light corresponding to an observation mode which is switched, in accordance with switching (or selection) of the observation mode for observing as an endoscope image by a user such as an operator.

In the endoscope apparatus 1, a user can switch the observation mode to a desired observation mode from an ordinary light observation mode for observing as an ordinary endoscope image (also called an ordinary light image), and a special light observation mode for observing as a special light image which gives image information differing from the ordinary light image. When the observation mode is switched to the ordinary light observation mode, the light source device 3 generates white (visible wavelength region) illumination light as ordinary illumination light, that is, illumination light of a broad band, and supplies it to the light guide 13. On the other hand, when the observation mode is switched to, for example, a narrow band light observation mode as the special light observation mode, the light source device 3 generates illumination light of a narrow band, and supplies it to the light guide 13.

The instruction of switching (or selection) of the normal light observation mode and the narrow band light observation mode can be performed by operation of a mode changeover switch 14a as a mode changeover portion formed by a scope switch or the like provided at the operation portion 8 of the endoscope 2, for example.

Since, the type of the corresponding endoscope image differs depending on switching of the observation mode, the switching portion of the observation mode has the function as the switching section for the type which switches (or selects) the type of the endoscope image.

In the present embodiment, when the observation mode or the type of the endoscope image is selected, the illumination light is changed to be the corresponding illumination light. But in embodiment 2 which will be described later, the illumination light is not changed even when the observation mode or the type of the endoscope image is switched. In the case of the latter, an image signal corresponding to the selected observation mode or type of the endoscope image is generated based on the (same) signal from the image pickup means by electric signal processing by the video processor 4 as the endoscope image processing device.

The instruction for switching the observation mode may be configured to be able to be performed by a foot switch in addition to the mode changeover switch 14a provided at the endoscope 2, and can be performed from a mode changeover switch 14b which is provided at an operation panel 17 of the video processor 4. Further, the switching instruction may be configured to be able to be performed by a keyboard or the like not illustrated.

A switching signal by the mode changeover switch 14a or the like is input into a control circuit 15 in the video processor 4. When the switching signal is input, the control circuit 15 controls a filter inserting and ejecting device 16, and selectively switches the ordinary illumination light and the narrow band illumination light.

Further, as will be described later, the control circuit 15 conducts control of switching section of the characteristic in an image processing section or a signal processing system configuring the video processor 4 being linked with the switching control of the illumination light supplied from the light source device 3 to the light guide 13.

By switching a part of the characteristic in the signal processing system by the switching instruction of the mode changeover switch 14a by a user, signal processing suitable for each of the ordinary light observation mode and the narrow band light observation mode can be performed.

Further, the operation panel 17 of the video processor 4 is provided with the mode changeover switch 14b, and an emphasis level changeover switch 19 as an emphasis amount switching section which performs switching of an emphasis level (or emphasis amount) when sharpness of the endoscope image or the image signal is emphasized, and the signals by the switches 14b and 19 are input into the control circuit 15. The mode changeover switch 14b has the same function as the mode changeover switch 14a.

Subsequently, as will be described later, the control circuit 15 is configured to conduct control of changing the correction characteristic of a tone by a tone correcting circuit section (in concrete, a γ circuit 50) provided in the video processor 4, and the emphasis characteristic of sharpness by an emphasis circuit section (in concrete, an emphasis circuit 48), for the endoscope image (or image signal) corresponding to switching by the switches 14b and 19.

The control circuit 15 forms control means which conducts control of changing the correction characteristic of a tone by the tone correcting circuit section in correspondence with at least one switching out of switching of the emphasis level and switching of the observation mode.

The configuration may be adopted, in which when switching of the emphasis level and switching of the observation mode are performed, the signals are directly received by the tone correcting circuit section without passing through the control circuit 50, and the tone correcting circuit section changes the correction characteristic of the tone.

The light source device 3 internally includes a lamp 20 which generates illumination light, and the lamp 20 generates illumination light including a visible region. The illumination light is incident on a diaphragm 22 after the illumination light is made illumination light near the wavelength band of substantially white light without infrared light which has been cut out by an infrared light cut filter 21. The diaphragm 22 has its passing light amount controlled by adjustment of an opening amount by means of a diaphragm driving circuit 23.

The illumination light which passes through the diaphragm 22 is incident on a condenser lens 25 through a narrow band filter 24 which is inserted in or ejected from an illumination optical path by the filter inserting and ejecting device 16 configured by a plunger or the like (at the time of the narrow band observation mode), or not through the narrow band filter 24 (at the time of the ordinary light observation mode), and is condensed by the condenser lens 25 to be incident on an incident end surface at the hand grip side of the light guide 13.

Figure 2:
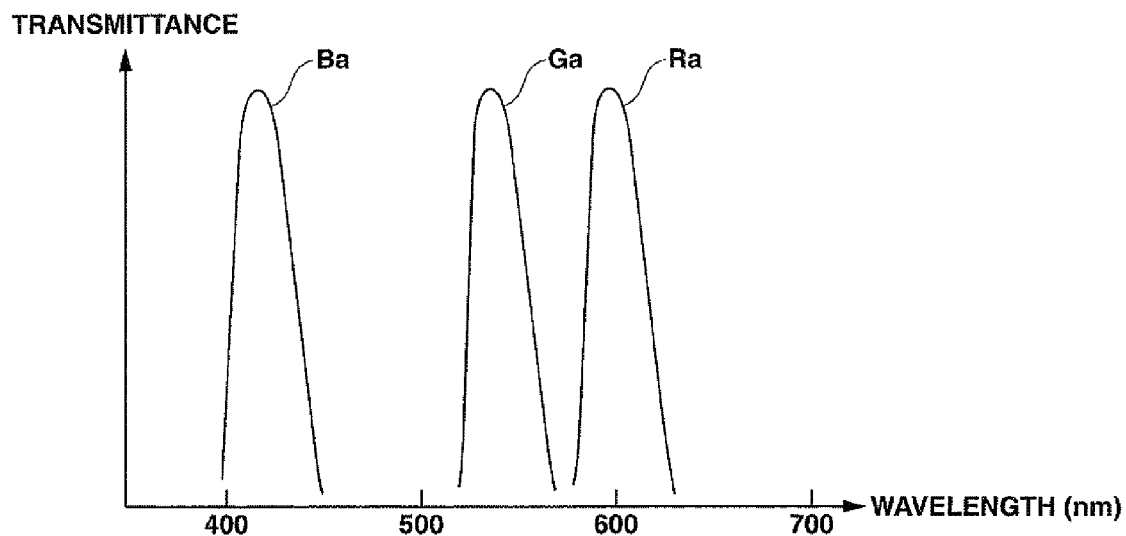
FIG. 2 is a characteristic chart showing a transmission property of a narrow-band filter.

FIG. 2 shows one example of the transmission property of the narrow band filter 24. The narrow band filter 24 shows a three-peak filter characteristic, and has narrow band transmission filter characteristic portions Ra, Ga and Ba which transmits light in narrow bands respectively in respective wavelength regions of red, green and blue, for example.

More specifically, the narrow band transmission filter characteristic portions Ra, Ga and Ba have center wavelengths of 600 nm, 540 nm and 420 nm respectively, and have band pass characteristics of their full widths at half maximum of 20 to 40 nm.

Accordingly, when the narrow band filter 24 is disposed in the illumination optical path, the illumination light of the three narrow bands which passes through the narrow band transmission filter characteristic portions Ra, Ga and Ba is incident on the light guide 13.

In contrast to this, when the narrow band filter 24 is not disposed in the illumination optical path, white light (of a visible wavelength region) is supplied to the light guide 13.

The illumination light from the light guide 13 is transmitted to a distal end surface of the light guide 13 by the light guide 13. The transmitted illumination light is irradiated outside from the distal end surface through an illumination lens 27 which is attached to an illumination window provided at a distal end portion 26 of the insertion portion 7. By the illumination light, the surface of a living body tissue of an affected portion or the like in a body cavity as a specimen.

The distal end portion 26 is provided with an observation window adjacent to the illumination window, and an objective lens 28 is attached to the observation window. The objective lens 28 forms an optical image in return light from a living body tissue. A charge coupled device (abbreviated as a CCD) 29 is disposed in an image forming position of the objective lens 28 as a solid image pickup device which forms image pickup means (image pickup section), and photoelectric conversion is performed by the CCD 29.

Figure 3:
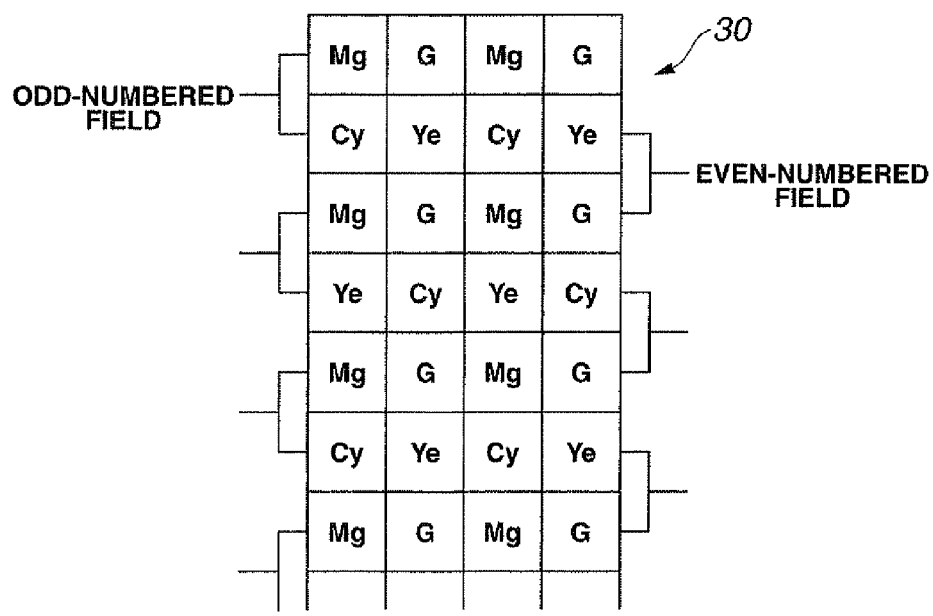
FIG. 3 is a diagram showing a layout example of respective filters used in a color separation filter.

A complementary color system filter shown in, for example, FIG. 3 is attached to an image pickup surface of the CCD 29 in each pixel unit as a color separation filter 30 which optically performs color separation.

In the complementary color system filter, in front of the respective pixels, color chips in four colors of magenta (Mg), green (G), cyan (Cy) and yellow (Ye) are disposed respectively such that Mg and G are alternately disposed in the horizontal direction, and in the vertical direction, the color chips are disposed respectively in the arrangement sequences of Mg, Cy, Mg, Ye, and G, Ye, G, Cy.

In the case of the CCD 29 using the complementary color system filter, the pixels in the two rows adjacent in the vertical direction are added and sequentially read, and at this time, the pixels are read by shifting the rows of the pixels between the odd-numbered fields and the even-numbered fields. Subsequently, by a Y/C separating circuit 37 at the rear stage side, a luminance signal and a color signal are generated as is known.

The above described CCD 29 is connected to one end of a signal line, and a signal connector to which the other end of the signal line is connected is connected to the video processor 4, whereby the CCD 29 is connected to a CCD driving circuit 31 and a correlated double sampling circuit (CDS circuit) 32 in the video processor 4.

By the signal processing system from the CDS circuit 32 through a D/A converting circuit 51, an image processing section which performs signal processing for generating an endoscope image from the output signal of the CCD 29 is formed. Further, the image processing section is provided with a γ circuit 50 which corrects a tone, an emphasis circuit 48 which emphasizing sharpness and the like.

Each endoscope 2 includes an ID generating section 33 which generates identification information (ID) peculiar to the endoscope 2. ID by the ID generating section 33 is input into the control circuit 15, and from the ID, the control circuit 15 identifies the type of the endoscope 2 connected to the video processor 4, the type, the number of pixels and the like of the CCD 29 equipped in the endoscope 2.

The control circuit 15 controls the CCD driving circuit 31 to drive the CCD 29 of the identified endoscope 2 properly.

The CCD 29 performs photoelectric conversion by application of a CCD drive signal from the CCD driving circuit 31. The image pickup signal subjected to photoelectric conversion is input into the CDS circuit 32. A signal of a base band, which is generated by a signal component being extracted from the image pickup signal by the CDS circuit 32, is input into the A/D converting circuit 34 to be converted into a digital signal, and is input into a brightness detecting circuit 35, and the brightness (average luminance of the signal) is detected.

The brightness signal detected by the brightness detecting circuit 35 is input into a light intensity adjustment circuit 36 and a light intensity adjustment signal for performing light intensity adjustment in accordance with a difference from the reference brightness (target value of light intensity adjustment) is generated. The light intensity adjustment signal is input into the diaphragm driving circuit 23 in the light source device 3, and the opening amount of the diaphragm 22 is adjusted so that the brightness becomes the reference brightness.

The digital signal output from the A/D converting circuit 34 is subjected to gain control by an automatic gain control circuit (abbreviated as an AGC circuit) 38 so that the signal level becomes a predetermined level, and thereafter, is input into the Y/C separating circuit 37. By the Y/C separating circuit 37, a luminance signal Yh, and color difference signals Cr (=2R−G) and Cb (=2B−G) of line sequence (as a color signal C in a wide meaning) are generated from the input signal.

The luminance signal Yh is input into a selector 39, and is also input into a first low pass filter (abbreviated as an LPF) 41 which restricts the pass band of a signal. The LPF 41 is set at a wide pass band in correspondence with the luminance signal Yh, and a luminance signal Y1 of a band corresponding to the pass band characteristic of the LPF 41 is input into a first matrix circuit 42.

Further, the color difference signals Cr and Cb are input into a (line sequential) synchronizing circuit 44 through a second LPF 43 which restricts a pass band of a signal.

In this case, the pass band characteristic of the second LPF 43 is changed by the control circuit 15 in accordance with the observation mode. More specifically, at the time of the normal light observation mode, the second LPF 43 is set at a band lower than that of the first LPF 41.

Meanwhile, at the time of the narrow band light observation mode, the second LPF 43 is changed to a band wider than the low band at the time of the normal light observation mode. For example, the second LPF 43 is set (changed) to a wide band substantially similarly to the first LPF 41. Thus, the second LPF 43 forms processing characteristic changing means which changes the processing characteristic restricting the pass band for the color difference signals Cr and Cb by being linked with selection of the observation mode.

The synchronizing circuit 44 generates the synchronized color difference signals Cr and Cb, and the color difference signals Cr and Cb are input into the first matrix circuit 42.

The first matrix circuit 42 converts the luminance signal Y1 and the color difference signals Cr and Cb into three primary color signals R1, G1 and B1, and the generated three primary color signals R1, G1 and B1 are input into a white balance circuit 45.

The first matrix circuit 42 is controlled by the control circuit 15, changes the values of matrix coefficients (determining the conversion characteristic) in accordance with the characteristic of the color separation filter 30 of the CCD 29 and the characteristic of the narrow band filter 24, converts the signals into the three primary color signals R1, G1 and B1 without color mixture or with color mixture substantially eliminated, and outputs the three primary color signals R1, G1 and B1.

For example, depending on the endoscope 2 actually connected to the video processor 4, the characteristic of the color separation filter 30 of the CCD 29 equipped in the endoscope 2 may differ, and the control circuit 15 changes the coefficient of the first matrix circuit 42 in accordance with the characteristic of the color separation filter 30 of the CCD 29 actually used based on the information of ID.

By doing as above, the image processing device can be suitably adapted to the case where the type of the image pickup device actually used differs. Thus, occurrence of a false color can be prevented, and conversion into the three primary color signals R1, G1 and B1 with (substantially) no color mixture can be performed.

By generating the three primary color signals R1, G1 and B1 with no color mixture, the image processing device has the operational effect of being capable of effectively preventing the color signal whose image is picked up under the narrow band light of a specific color from becoming difficult to discriminate due to the color signal whose image is picked up under the narrow band light of another color especially at the time of the narrow band light observation mode.

From the three primary color signals R1, G1 and B1 which are input into the white balance circuit 45, three primary color signals A2, G2 and B2 which are adjusted to be white-balanced are generated by the white balance circuit 45.

The three primary color signals R2, G2 and B2 output from the white balance circuit 45 are input into a second matrix circuit 46, and are converted into a luminance signal and color difference signals R-Y and B-Y by the second matrix circuit 46.

In this case, the control circuit 15 sets matrix coefficients of the second matrix circuit 46 so that the three primary color signals A2, G2 and B2 are simply converted into a luminance signal Y and the color difference signals R-Y and B-Y at the time of the ordinary light observation mode.

At the time of the narrow band light observation mode, the control circuit 15 changes the matrix coefficients of the second matrix circuit 46 from the value at the time of the ordinary light observation mode so that a luminance signal Ynbi with a ratio (weighting) to the B signal especially increased and the color difference signals R-Y and B-Y are generated from the three primary color signals X2, G2 and B2.

The conversion formula in this case is as follows when matrixes A and K each with three rows and three columns are used.

$$\begin{pmatrix} Ynbi \\ R-Y \\ B-Y \end{pmatrix} = A * K * \begin{pmatrix} R2 \\ G2 \\ B2 \end{pmatrix} \quad (1)$$

$$K = \begin{pmatrix} 0 & k1 & 0 \\ 0 & 0 & k2 \\ 0 & 0 & k3 \end{pmatrix}$$

Here, K is constituted of, for example, three real number components k1 to k3 (the other components are zero), and by the conversion formula such as formula (I), weighting of the color signals of a and B is large with respect to the color signal of R, and especially, weighting (ratio) of the color signal of B is the largest. In other words, the color signal of R of a long wavelength is suppressed, and the color signal of B of a short wavelength side is emphasized.

A is a matrix (array) for converting the RGB signals into the Y color difference signals, and the known arithmetic coefficients as follows are used.

$$A = \begin{pmatrix} 0.299 & 0.587 & 0.114 \\ -0.299 & -0.587 & 0.886 \\ 0.701 & -0.587 & -0.114 \end{pmatrix} \quad (2)$$

The luminance signal Ynbi which is output from the second matrix circuit 46 is input into the selector 39. Switching of the selector 39 is controlled by the control circuit 15. Specifically, at the time of the ordinary light observation mode, the luminance signal Yh is selected, whereas at the time of the narrow band light observation mode, the luminance signal Ynbi is selected. In FIG. 1, the luminance signal Yh or Ynbi which is selected and output from the selector 39 is expressed by a luminance signal Ysel.

The color difference signals R-Y and B-Y which are output from the second matrix circuit 46 are input into an enlargement interpolation circuit 47 together with the luminance signal Yh or Ynbi (namely, Ysel) which passes through the selector 39.

The luminance signal Ysel to which enlargement processing is applied by the enlargement interpolation circuit 47 is input into the γ circuit 50 as a tone correcting circuit section which performs γ correction of an endoscope image (or an image signal), that is, tone correction of an endoscope image.

The luminance signal Ysel to which the γ correction processing is applied by the γ circuit 50 is input into the emphasis circuit 48 as an emphasis circuit section which performs processing of emphasis of the sharpness of an endoscope image (or an image signal).

The luminance signal Ysel to which the processing of emphasis of the sharpness is applied by the emphasis circuit 48 is input into a third matrix circuit 49. Further, the color difference signals R-Y and B-Y to which enlargement processing is applied by the enlargement interpolation circuit 47 are input into the third matrix circuit 49 after being subjected to γ correction, that is, tone correction by the γ circuit 50.

Subsequently, after the color difference signals R-Y and B-Y are converted into three primary signals R, G and B by the third matrix circuit 49, the three primary signals R, G and B are converted into analogue three primary signals R, G and B by the D/A converting circuit 51 and are output to a monitor 5 as display means of the endoscope image from a video signal output end.

The control circuit 15 performs control of setting of change of the characteristic of the LPF 43, setting of change of the matrix coefficients of the first matrix circuit 42 and the second matrix circuit 46, selection of the luminance signals Yh/Ynbi of the selector 39, and switching of a γ_table value in the γ circuit 50 in correspondence with switching or selection of the observation mode by operation of the mode changeover switch 14a or 14b.

Further, the control circuit 15 controls the operation of the filter inserting and ejecting device 16 of the light source device 3 in accordance with switching of the observation mode. Further, the control circuit 15 performs gain setting of the white balance circuit 45 at the time of white balance adjustment.

Figure 4:
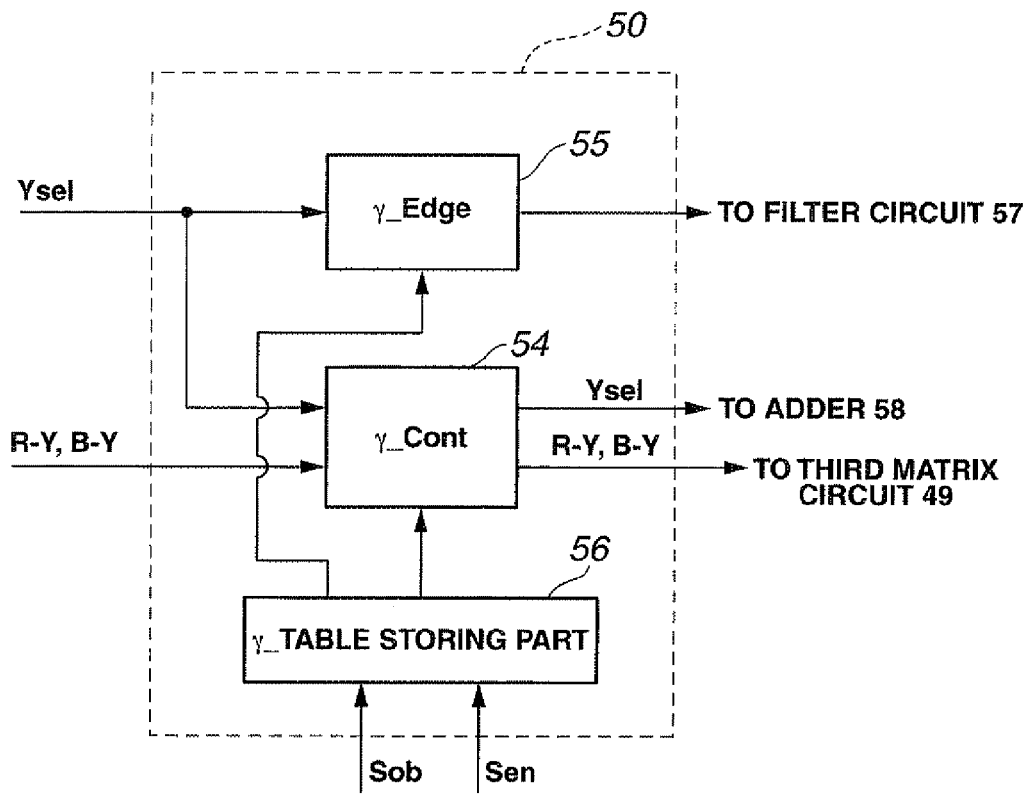
FIG. 4 is a block diagram showing a configuration of a γ circuit of FIG. 1.

The above described γ circuit 50 has a configuration as shown in FIG. 4. The luminance signal Ysel is input into a γ_Contrast circuit (hereinafter, abbreviated as a γ_Cont circuit) 54 which performs tone correction of the entire endoscope image corresponding to the luminance signal Ysel (configures a first tone correction circuit section), and a γ_edge circuit 55 which performs tone correction corresponding to emphasis of the contour of the endoscope image (configures a second tone correction circuit section).

Further, the color difference signals R-Y and B-Y are input into only the γ_Cont circuit 54 which also performs tone correction corresponding to the color difference signals.

For the γ_Cont circuit 54 and the γ_Edge circuit 55, γ_table values for the γ_Cont and γ_Edge which are stored in a γ_table storing section 56 are set.

In the present embodiment, for example, the γ_table value for the γ_Cont is not changed with respect to switching of the observation mode and switching (change) of the emphasis level and is commonly used.

The γ_Cont circuit 54 performs tone correction of the luminance signal Ysel and the color difference signals R-Y and B-Y which are input, in accordance with the γ_table value for the γ_CSont.

In contrast to this, the γ_table value for the γ_Edge which differs in the input and output characteristic is set in any switching of switching of the observation mode and switching of the emphasis level, and tone correction is performed for the input luminance signal Ysel, in accordance with the γ_table value for the γ_Edge which is actually set.

Accordingly, in the γ_table storing section 56, the γ_table value for the γ_Edge corresponding to the observation mode, and the γ_table value for the γ_Edge corresponding to the emphasis level selected by switching are stored in advance. When an observation mode setting instruction signal Sob is input into the γ_table storing section 56 from the control circuit 15 in correspondence with the observation mode selected by the switching operation by the user, the γ_table value for the γ_Edge corresponding to the observation mode is read, and is set in the γ_Edge circuit 55.

Thus, in the γ circuit 50 in the present embodiment, by changing the data stored in lookup table means or a ROM in accordance with switching of the observation mode and the emphasis level, even when the emphasis level or the like is changed significantly, the input and output characteristic can be realized by being adapted to the change. Noise which easily becomes conspicuous in the low intensity or the like is effectively suppressed.

Further, the control circuit 15 controls the filter coefficient which is used when performing filter processing for emphasizing the sharpness by the emphasis circuit 48 in correspondence with the observation mode selected by the user, as will be described later.

Further, when an emphasis level setting instruction signal Sen is input into the γ_table storing section 56 from the control circuit 15 in correspondence with the emphasis level selected by the user, the γ_table value for the γ_Edge corresponding to the emphasis level and the selected observation mode is read, and is set in the γ_Edge circuit 55, similarly.

The γ_Edge circuit 55 performs tone correction for the input luminance signal Ysel in accordance with the γ_table value for the γ_Edge which has been set.

Figure 5:
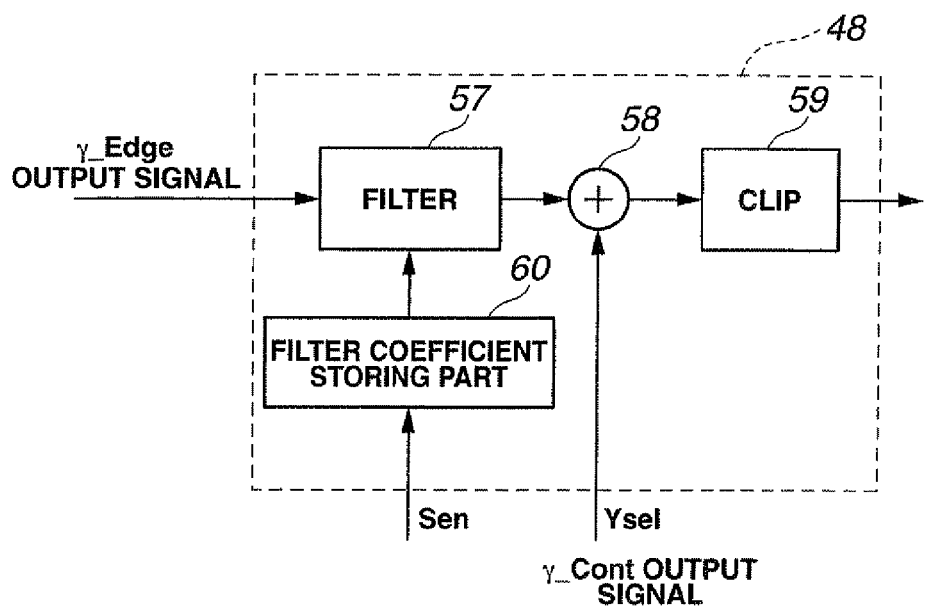
FIG. 5 is a block diagram showing a configuration of an emphasis circuit of FIG. 1.

An output signal of the γ_Edge circuit 55 is input into a filter circuit 57 in the emphasis circuit 48 as shown in FIG. 5. The signal which is input into the filter circuit 57 is input into an adder 58 after filter processing for emphasizing sharpness is applied to the signal by, for example, a spatial filter (for example, 9 by 9) in the filter circuit 57.

The luminance signal Ysel output by the γ_Cont circuit 54 is also input into the adder 58, and both output signals from the filter circuit 57 and the γ_Cont circuit 54 are added and output from the adder 58.

An output signal of the adder 58 is input into a clipping circuit 59, and is clipping-processed by the clipping circuit 59 so as to be in a predetermined output range, and is output to the third matrix circuit 49 of FIG. 1. For example, the clipping circuit 59 clips the output signal to the data value within 0 to 1023 when the number of input bits of the third matrix circuit 49 into which the output signal is input is 10 bits.

Further, a filter coefficient storing section 60 which stores filter coefficients corresponding to a plurality of emphasis levels in advance is provided in the emphasis circuit 48, and by the above described emphasis level setting instruction signal Sen being input into the filter coefficient storing section 60, the filter coefficient storing section 60 sets the filter coefficient corresponding to the instruction signal Sen to the filter circuit 57. Subsequently, the filter circuit 57 performs filter processing with the filter coefficient actually set.

Figure 6A:
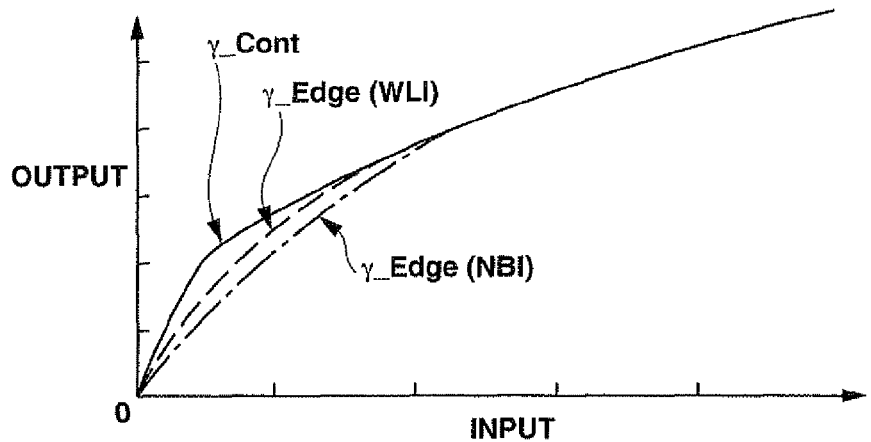
FIG. 6A is a characteristic chart showing input and output characteristics of a γ_Edge circuit set in correspondence with observation modes which are switched, with an input and output characteristic of a γ_Cont circuit.

FIG. 6A shows input and output characteristics of the γ_Edge circuit 55 which are set in correspondence with the switched observation modes together with the input and output characteristic of the γ_Cont circuit 54.

In FIG. 6A, the input and output characteristic of the γ_Edge circuit 55 in the case of the ordinary light observation mode is shown by γ_Edge (WLI), and the input and output characteristic of the γ_Edge circuit 55 in the case of the narrow band light observation mode is shown by γ_Edge NBI). Further, the input and output characteristic of the γ_Cont circuit 54 is common to both the modes, and is shown simply by γ_Cont.

As is found out from FIG. 6A, in the ordinary light observation mode, in the low intensity portion (left side portion of the horizontal axis), the γ_Edge circuit 55 is set at the characteristic that outputs a value smaller than the value of the γ_Cont circuit 54.

Further, in the narrow band light observation mode, the γ_Edge circuit 55 is set at the characteristic that outputs a value smaller than the case of the ordinary light observation mode in the low intensity portion.

Thereby, in the low intensity portion of an image, the intensity of the sharpness emphasis signal extracted by the filter circuit (see FIG. 5) is reduced, and therefore, noise in the low intensity portion at the time of gain-up when the shortage of the light amount in the narrow band light observation mode is compensated by the AGC circuit 38 can be suppressed.

Namely, in the narrow band light observation mode, the band of the illumination light is limited as compared with the case of the ordinary light observation mode, and therefore, as it is, the light amount becomes small as compared with the ordinary light observation mode, and the light amount sometimes becomes insufficient even in the state where the diaphragm 22 is totally opened. In this case, an AGC function of the AGC circuit 38 operates, and the shortage of the light amount is compensated by gain up by the AGC circuit 38.

In the high intensity portion in the image after the compensation is performed, S/N is relatively high. However, in the low intensity portion, S/N is low. Therefore, noise is especially conspicuous, and the noise sometimes becomes more conspicuous due to the emphasis processing by the emphasis circuit 48.

In the present embodiment, by setting the input and output characteristic of the γ_Edge circuit 55 as in FIG. 6A, the intensity of the emphasis signal in the low intensity portion is reduced as described above, and therefore, amplification of the noise by emphasis processing can be suppressed.

Figure 6B:
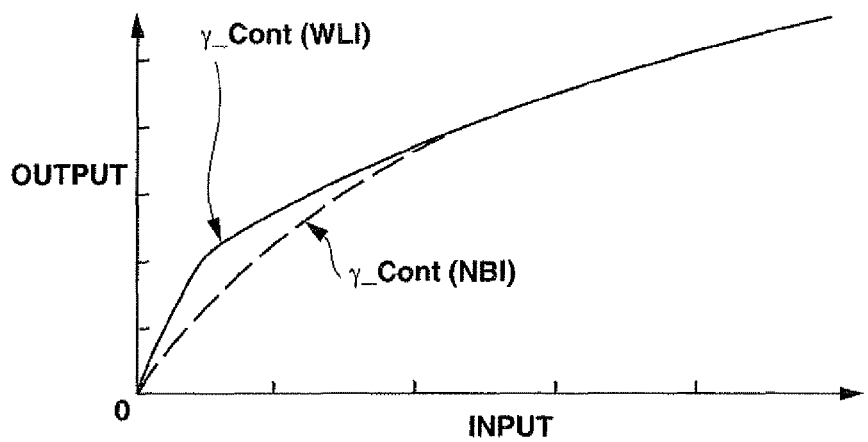
FIG. 6B is a characteristic chart showing input and output characteristics of the γ_Cont circuit in the case of an ordinary light observation mode and in the case of a narrow band light observation mode.

In the present embodiment, the γ_Cont circuit 54 is commonly used in both the modes, but its characteristic may be changed in accordance with selection of the observation mode. FIG. 6B shows characteristic examples which are set in such a case.

In FIG. 6B, the input and output characteristic of the γ_Cont circuit 54 in the case of the ordinary light observation mode is shown by γ_Cont (WLI), and the input and output characteristic of the γ_Cont circuit 54 in the case of the narrow band light observation mode is shown by γ_Cont (NBI).

Here, the γ_Cont (WLI) is the same input and output characteristic as the γ_Cont of FIG. 6A, and the γ_Cont (NBI) is set at the characteristic that outputs a value smaller than the γ_Cont (WLI) in the low intensity portion.

In this case, in the γ circuit 50 of FIG. 1, when the observation mode setting instruction signal Sob is input into the γ_table storing section 56 from the control circuit 15 in correspondence with the observation mode selected by the user, the γ_table value for the γ_Cont corresponding to the observation mode is read, and the γ_table value is set in the γ_Cont circuit 54.

By switching (changing) the input and output characteristic (γ_table value) in accordance with the observation mode as the input and output characteristic of the γ_Edge circuit 55, noise in the low intensity portion of the narrow band light observation mode accompanying gain up can be suppressed.

Figure 6C:
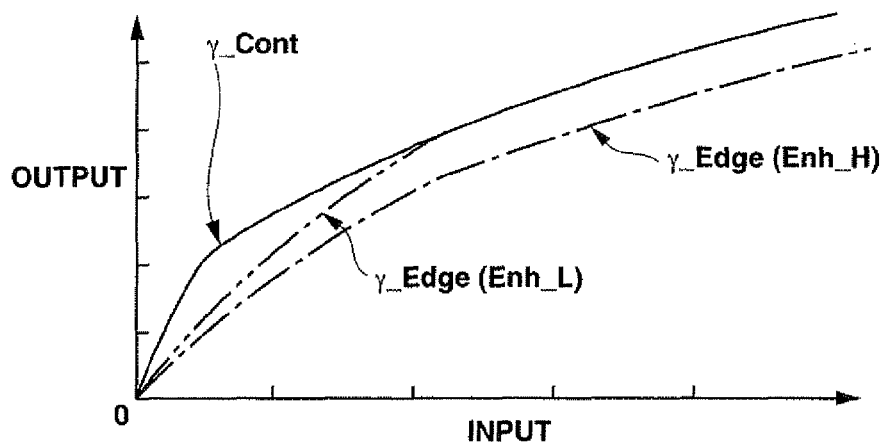
FIG. 6C is a characteristic chart showing an example in which the input and output characteristics of the γ_Edge circuit are switched by switching of both the observation mode and emphasis level with the case of the narrow band light observation mode.

FIG. 6C shows the characteristic examples in which the input and output characteristic of the γ_Edge circuit 55 is switched in accordance with both switching of the observation mode and switching of the emphasis level in the case of the narrow band light observation mode. Here, the input and output characteristic of the γ_Cont circuit 54 shown in FIG. 6A for reference is also shown.

As the input and output characteristic of the γ_Edge circuit 55, the case of making the emphasis level large is shown by γ_Edge (Enh_H), and the case of making the emphasis level small is shown by γ_Edge (Enh_L). The magnitude of the emphasis level can be selected by the above described emphasis level changeover switch 19.

As is understood from the characteristic of the γ_Edge (Enh_H) shown in FIG. 6C, when the filter coefficient which increases the degree of the emphasis amount by increasing the emphasis level is set, the γ table which becomes an output value smaller than the input and output characteristic of the γ_Cont circuit 54 is set to be applied over the entire luminance region.

In contrast to this, the characteristic of the γ_Edge (Enh_L) has an output value smaller than the input and output characteristic of the γ_Cont circuit 54 in only the low intensity side.

Thereby, in the low intensity portion, unnecessary emphasis of noise can be suppressed, and in the high intensity portion, overshoot and undershoot of the edge portion can be reduced. Therefore, excessive emphasis can be suppressed.

Thus, in the present embodiment, when correction processing of the tone for the image signal corresponding to an endoscope image is performed, the processing is performed dividing the processing for tone correction close to the ordinary tone correction which performs tone correction for the entire image signal and the processing for emphasis of sharpness. In at least the processing for emphasis of sharpness, the input and output characteristic is changed in accordance with switching of the emphasis level of the sharpness and switching of the observation mode.

In this case, the configuration is adopted, in which the inclination of the tone correction curve in the low intensity portion is set to be smaller as the emphasis level of the sharpness is higher, or in the case of the narrow band light observation mode in which the band is limited, and therefore, visually conspicuous noise in the low intensity portion can be effectively reduced.

Further, the input and output characteristic at the time of processing for emphasis of sharpness is changed in accordance with switching of the emphasis level and the observation mode as described above. Therefore, when, for example, the emphasis level is changed in a wide range or in multiple stages, the image processing device can be properly adapted to the change, as compared with the case in which the input and output characteristic is not changed.

Further, the input and output characteristic of tone correction for the above described processing for tone correction is changed in accordance with switching of the observation mode. In this case, at the time of the narrow band light observation mode, the input and output characteristic of tone correction is set at the input and output characteristic for outputting a smaller value in the low intensity portion. Thereby, noise in the low intensity portion which occurs by gain up for making up for brightness shortage can be suppressed more effectively.

Further, the present embodiment can effectively reduce noise which is visually conspicuous, with the simple configuration.

Further, by switching the input and output characteristic by the lookup table in accordance with switching of the emphasis level of sharpness and switching of the observation mode, high-speed processing can be performed.

As the above described embodiment 1, the example which is applied to the case of the synchronous type is described, but the present invention can be also applied to the case of a frame sequential type endoscope apparatus as follows.

In the frame sequential endoscope apparatus, frame sequential illumination is performed by irradiating R, G and B lights or a plurality of narrow band lights sequentially to a subject side, and under the frame sequential illumination, image pickup is performed in the frame sequential manner by using a monochromic image pickup device (which does not have a color separation filter).

Figure 7:
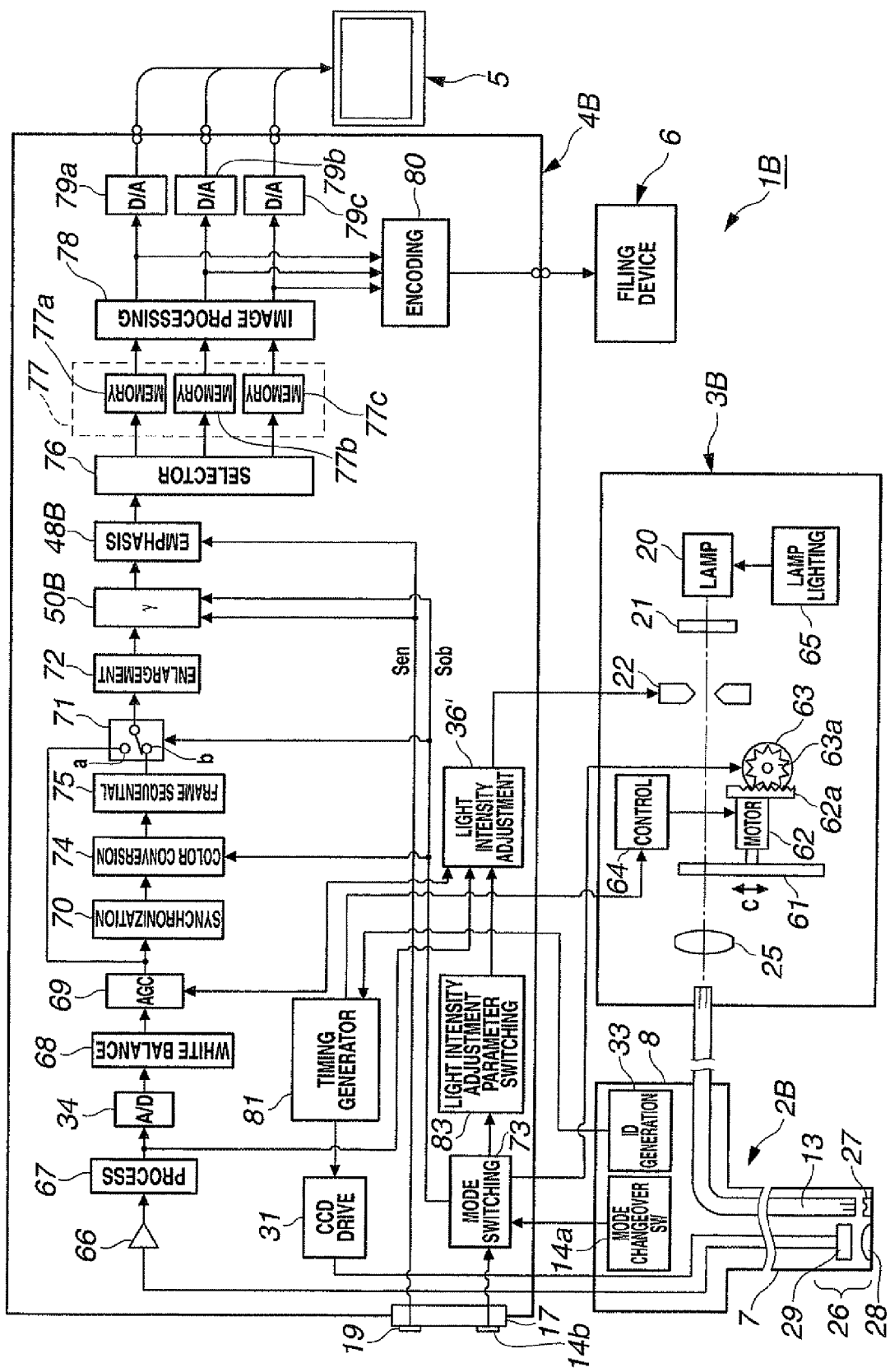
FIG. 7 is a block diagram showing an entire configuration of a frame sequential type endoscope apparatus of a modified example.

A frame sequential type endoscope apparatus 1B shown in FIG. 7 is configured by an endoscope 2B, a light source device 3B, a video processor 4B, a monitor 5 and a filing device 6 which records an endoscope image.

In the endoscope 2B, a monochromic CCD 29 which does not have the color separation filter 30 in the endoscope 2 of FIG. 1 is used.

Further, the light source device 3B is provided with a rotary filter 61 which converts the illumination light by the lamp 20 into frame sequential light, a motor 62 which rotationally drives the rotary filter 61, a moving motor 63 which moves a holding plate 62a which holds the motor 62 in a direction orthogonal to the optical path, and a control circuit 64 which rotates the motor 62 at a constant speed, instead of the filter inserting and ejecting device 16 and the filter 24 in the light source device 3 of FIG. 1. A lamp lighting circuit 65 supplies lamp lighting power to the lamp 20 to light the lamp 20.

The holding plate 62a is provided with, for example, a rack portion, and the rack portion is meshed with a pinion gear 63a provided at a rotary shaft of the moving motor 63. When the holding plate 62a is moved as shown by the arrow C in FIG. 7 by the moving motor 63, the rotary filter 61 is also moved with the motor 62.

Figure 8:
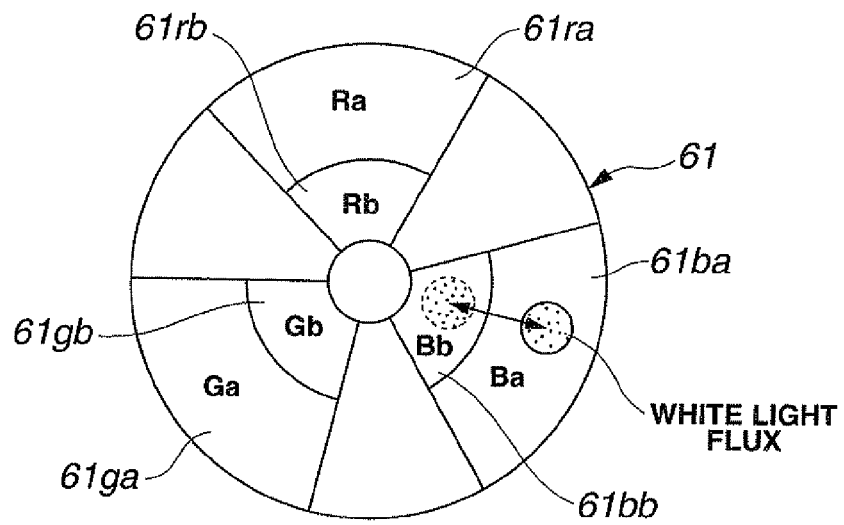
FIG. 8 is a front view showing a configuration of a revolving filter.

The rotary filter 61 is configured to be in a disk shape and is of a double structure with a center as a rotary shaft as shown in FIG. 8.

Figure 9:
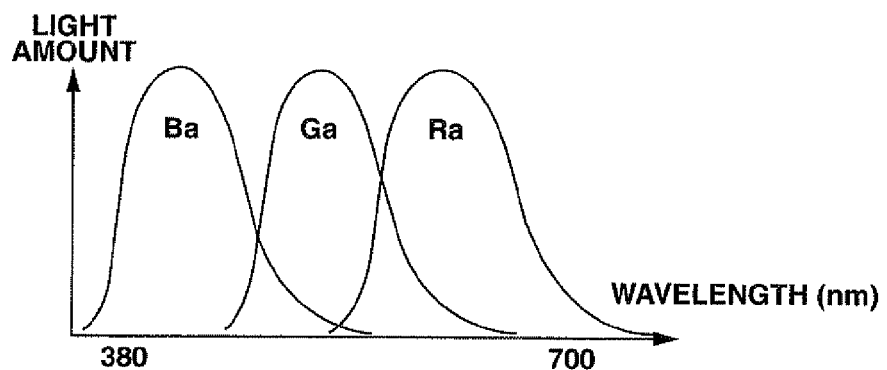
FIG. 9 is a characteristic chart showing transmission properties of respective filters configuring a first filter group disposed in an outer side of FIG. 8.

An Ra filter 61ra, a Ga filter 61ga, and a Ba filter 61ba, which configure a first filter group for outputting frame sequential light with overlapping (wide band) spectral characteristics suitable for color reproduction as shown in FIG. 9, are disposed at a circumferential portion at an outer side with a large diameter. In FIG. 9, the wavelength bands Ra, Ga and Ba which are transmitted by the Ra filter 61ra, the Ga filter 61ga and the Ba filter 61ba are shown.

Further, an Rb filter 61rb, a Gb filter 61gb and Rb filter 61bb, which configures a second filter group for outputting frame sequential light of a narrow band with discrete spectra characteristics capable of extracting tissue information at a desired depth in the vicinity of the surface layer of a living body tissue, are disposed at a circumferential portion at an inner side.

Figure 10:
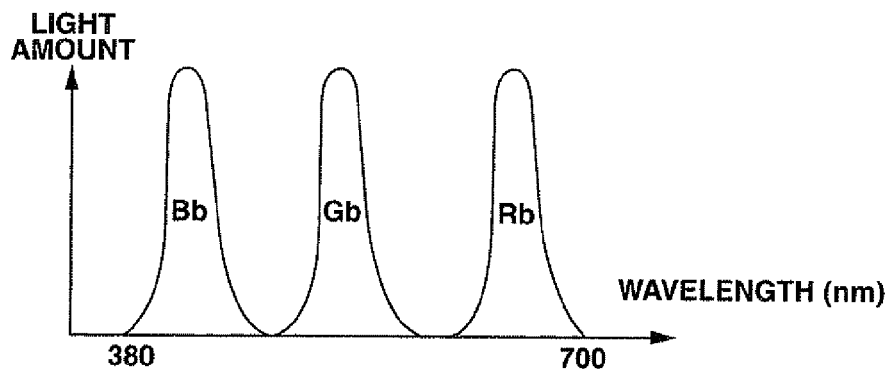
FIG. 10 is a characteristic chart showing transmission properties of respective filters configuring a second filter group disposed in an inner side of FIG. 8.

In FIG. 10, wavelength bands Rb, Gb and Bb which are transmitted respectively by the Rb filter 61rb, the Gb filter 61gb and the Bb filter 61bb are shown.

The moving motor 18 is normally rotated or reversed by a drive signal which is output from a mode switching circuit 73 in accordance with an instruction signal for mode switching of the mode changeover switch 14a or 14b by the user, whereby the first filter group or the second filter group can be disposed on the optical path in accordance with the observation mode.

When the first filter group is disposed on the optical path, ordinary frame sequential light of red, green and blue, that is, the frame sequential light of the wide band of Ra, Ga and Ba shown in FIG. 9 is obtained, which corresponds to the ordinary light observation mode in which an ordinary light observation image is obtained.

In contrast to this, when the second filter group is disposed on the optical path, frame sequential light of a narrow band is obtained, which corresponds to the narrow band light observation mode (NBI mode) in which a narrow band light observation image is obtained. FIG. 8 shows the positions of light fluxes in the case in which the first filter group and the second filter group are disposed on the optical path.

Further, the video processor 413 has the CCD driving circuit 31, and the signal, which is photoelectrically converted by the CCD 29 by application of the CCD drive signal by the CCD driving circuit 31, is amplified by a preamplifier 66 in the video processor 4B, and thereafter, is input into the A/D converting circuit 34 and is input into a light intensity adjustment circuit 36' through a process circuit 67 which performs correlation double sampling, noise removal and the like. The light intensity adjustment circuit 36' has the functions of the brightness detecting circuit 35, the light intensity adjustment circuit 36 and the diaphragm driving circuit 23 of FIG. 1.

After being converted into image data of a digital signal from an analogue signal by the A/D converting circuit 34, the signal is input into a white balance circuit 68, and after processing of white balance is performed, the signal is input into an AGC circuit 69 and amplified to a predetermined level.

The light intensity adjustment operation in the illumination light amount by the diaphragm 22 of the light source device 3 is preferentially performed the AGC function by the AGC circuit 69. After the opening of the diaphragm 22 reaches the full state, the AGC circuit 69 amplifies the signal so as to increase the signal level by the amount of shortage even in the full state, based on the information of the fall state.

Further, the light intensity adjustment circuit 36' generates a light intensity adjustment signal for adjusting the opening amount of the diaphragm 22 of the light source device 3 and controls the illumination light amount to a proper illumination light amount from the output signal of the process circuit 67.

The output date of the above described AGC circuit 69 is input into a synchronizing circuit 70 which converts a frame sequential signal into a synchronized signal, and is input into an enlargement circuit 72 via a changeover switch 71. In the changeover switch 71, by the operation of the mode changeover switch 14a, a contact a is selected at the time of the normal light observation mode via a mode switching circuit 73, and a contact b is selected at the time of the narrow band light observation mode.

The signal data which is synchronized by the synchronizing circuit 70 is input into a color converting circuit 74, and processing of color conversion is performed by the color converting circuit 74. The color converting circuit 74 performs color conversion of the synchronized RGB image information by the matrix of 3 by 3. Thereby, visibility of the image information reproduced in the narrow band light observation mode is improved.

As the conversion formula for color conversion into R', G' and B' from RGB in this case, a matrix K with three rows and three columns in formula (I) is used for conversion.

As described above, K is constituted of, for example, three real number components k1 to k3 (the other components are zero). By conversion in accordance with the matrix K, weighting (ratio) of the color signal of B in the RGB color signals is made the largest, the color signal of R which is imaged by the transmitted light of the R2 filter with the largest wavelength is suppressed, and the color signal of B at the short wavelength side is emphasized so that the signals are displayed as an RGB color image.

The output signals (R', G' and B', but described by using R, G, B for simplification) of the color converting circuit 74 are input into a frame sequential circuit 75.

The frame sequential circuit 75 is configured by a frame memory, and sequentially reads the image data of R, G, B which are simultaneously stored as color component images, thereby converting the image data into frame sequential image data. The frame sequential image data R, G and B are input into the enlargement circuit 72 through the changeover switch 71, are subjected to enlargement interpolation processing, and thereafter, are input into a γ circuit 50B.

γ correction is performed for the input frame sequential signal data of R, G and B by the γ circuit 50B. The γ circuit 50B has the configuration corresponding to the γ circuit 50 shown in FIG. 4 in embodiment 1. In embodiment 1, the luminance signals Ysel, R-Y and B-Y are input into the γ circuit 50, but in the present modified example, frame sequential R, G and B signals are input.

In this case, instead of the luminance signal Ysel shown in FIG. 4, the frame sequential R, G and B signals are input, and the portion where the color difference signals R-Y and B-Y are input into the γ_Cont circuit 54, and the portion where the color difference signals R-Y and B-Y are output from the γ_Cont circuit 54 to the third matrix circuit 49 are eliminated.

The output signal of the γ circuit 50B is input into an emphasis circuit 48B, and after sharpness emphasis processing is performed by the emphasis circuit 48B as in embodiment 1, the output signal is input into a synchronizing circuit 77 through a selector 76.

In the present embodiment, the output signal of the γ_Edge circuit 55 shown in FIG. 4 is input into the filter circuit 57 (see FIG. 5) in the emphasis circuit 48B. Further, the γ_Cont circuit 54 in FIG. 4 outputs the frame sequential R, G and B signals to the adder 58 (see FIG. 5) in the emphasis circuit 48B, instead of the luminance signal Ysel.

The above described synchronizing circuit 77 is formed by, for example, three memories 77a, 77b and 77c.

The signal data which is synchronized by the synchronizing circuit 77 is input into an image processing circuit 78, and after image processing such as correction of out-of-color registration of a moving image or the like is applied to the signal data, the signal data is input into D/A converting circuits 79a, 79b and 79c and an encoding circuit 80. The signal data is converted into the analogue video signals by the D/A converting circuits 79a, 79b and 79c, and thereafter, is input into the monitor 5.

The monitor 5 displays an endoscope image corresponding to a video signal which is input. Further, the endoscope image signal compressed by the encoding circuit 80 is input into the filing device 6, and recorded. Further, in the video processor 4B, a timing generator 81 is provided, in which a synchronized signal which is synchronized with the rotation of the rotary filter 61 from the control circuit 64 of the light source device 3 is input, and the timing generator 81 outputs various types of timing signals synchronized with the synchronized signal to the above described respective circuits.

The ID of the ID generating section 33 is input into the timing generator 81, and even when the number of pixels of the CCD 29 differs, the timing generator 81 sends the control signal and the timing signal for driving the CCD 29 based on the ID to the CCD driving circuit 31.

Further, the output signal of the mode changeover switch 14a which performs instruction of mode switching and is provided in the endoscope 2B is input into the mode switching circuit 73 in the video processor 4B.

The mode switching circuit 73 outputs the control signal corresponding to the instruction signal for mode switching, which is input, to a light intensity adjustment parameter switching circuit 83 and the moving motor 63 of the light source device 3, and controls switching of the changeover switch 71 and the input and output characteristic of the γ circuit 50B.

The light intensity adjustment parameter switching circuit 83 outputs a light intensity adjustment parameter corresponding to the first filter group or the second filter group of the rotary filter 61 to the light intensity adjustment circuit 36', and the light intensity adjustment circuit 36' controls the diaphragm 22 of the light source device 3 based on the control signal from the mode switching circuit 73 and the light intensity adjustment parameter from the light intensity adjustment parameter switching circuit 83, and conducts control to provide proper brightness.

Further, when predetermined brightness is not achieved by only the control of the diaphragm 22, the light intensity adjustment parameter switching circuit 83 sends a control signal for operating AGC of the AGC circuit 69, and controls the AGC circuit 69 so that the predetermined brightness is achieved.

Specifically, the light intensity adjustment circuit 36' sends a control signal, which is calculated based on the output signal of the process circuit 67 and the gain value transmitted from the AGC circuit 69 and is for making the brightness of the image have a predetermined value, to the AGC circuit 69.

In the present modified example, the observation mode can be switched by operating the mode changeover switches 14a and 14b, and the input and output characteristics of the γ_Edge circuit 55 and the γ_Cont circuit 54 (see FIG. 4) of the γ circuit 50B are properly set in accordance with the ordinary light observation mode or the narrow band light observation light which is switched and set.

Further, when the emphasis level is switched by operation of the emphasis level changeover switch 19, the input and output characteristic of the γ_Edge circuit 55 of the γ circuit 50B is properly set in accordance with the emphasis level.

When the observation mode is switched from the ordinary light observation mode to the narrow band light observation mode as in the case of embodiment 1 in the present modified example, the input and output characteristic of the γ_Edge circuit 55 of the γ circuit 50B in the narrow band light observation mode outputs a lower value (smaller output value) at the low intensity portion side than in the case of the ordinary light observation mode as shown in FIG. 6A.

Further, when the emphasis amount is made large by increasing the emphasis level as shown in FIG. 6C, as the emphasis amount becomes larger, the input and output characteristic of the γ_Edge circuit 55 is switched to the characteristic which outputs a smaller value.

Accordingly, as the effect of the present modified example, the effect similar to embodiment 1 can be obtained.

The input and output characteristic of the γ_Edge circuit 55 corresponding to switching of the emphasis level in the present modified example may be set as in FIG. 6A.

Specifically, as the emphasis level increases, the input and output characteristic is switched to the input and output characteristic which outputs a smaller value in only the low intensity portion. When the frequency characteristic of emphasis which is applied in the filter circuit 57 reduces overshoot and undershoot in the high intensity portion, noise in the low intensity portion is reduced, and suppress of the emphasis effect of high intensity can be reduced.

Further, in the case of switching of the emphasis level, the data amount can be reduced by commonality of data when the characteristic as shown in FIG. 6A is adopted.

(Embodiment 2)

Next, embodiment 2 of the present invention will be described with reference to FIG. 11. The present embodiment is an embodiment in which an image (called a pseudo-narrow band image, or a spectral image) corresponding to a narrow band image obtained in illumination of (synchronizing type) narrow band light is obtained in the state of ordinary illumination light without using illumination light of a narrow band. Since the configuration does not use the illumination light of the narrow band in embodiment 1, the background will be described first.

Japanese Patent Application Laid-Open Publication No. 2003-93336 discloses an endoscope apparatus for making the running state or the like of a blood vessel with respect to the depth direction in the vicinity of a mucosal surface layer more visible without using narrow band light. The prior example has a simple configuration, but the spectral image corresponding to the narrow band image which is picked up in narrow band light is generated by a numerical operation. Therefore, the signal level of the spectral image becomes low, and S/N becomes low, as a result of which, noise tends to be conspicuous.

Therefore, the configuration of the present embodiment 2 is adopted for the purpose of providing an image processing device for an endoscope and an endoscope apparatus capable of displaying a sharpness emphasis processing image with less noise even when a spectral image signal is generated likewise from the signal of the image picked up under ordinary visible light without using narrow band light.

Figure 11:
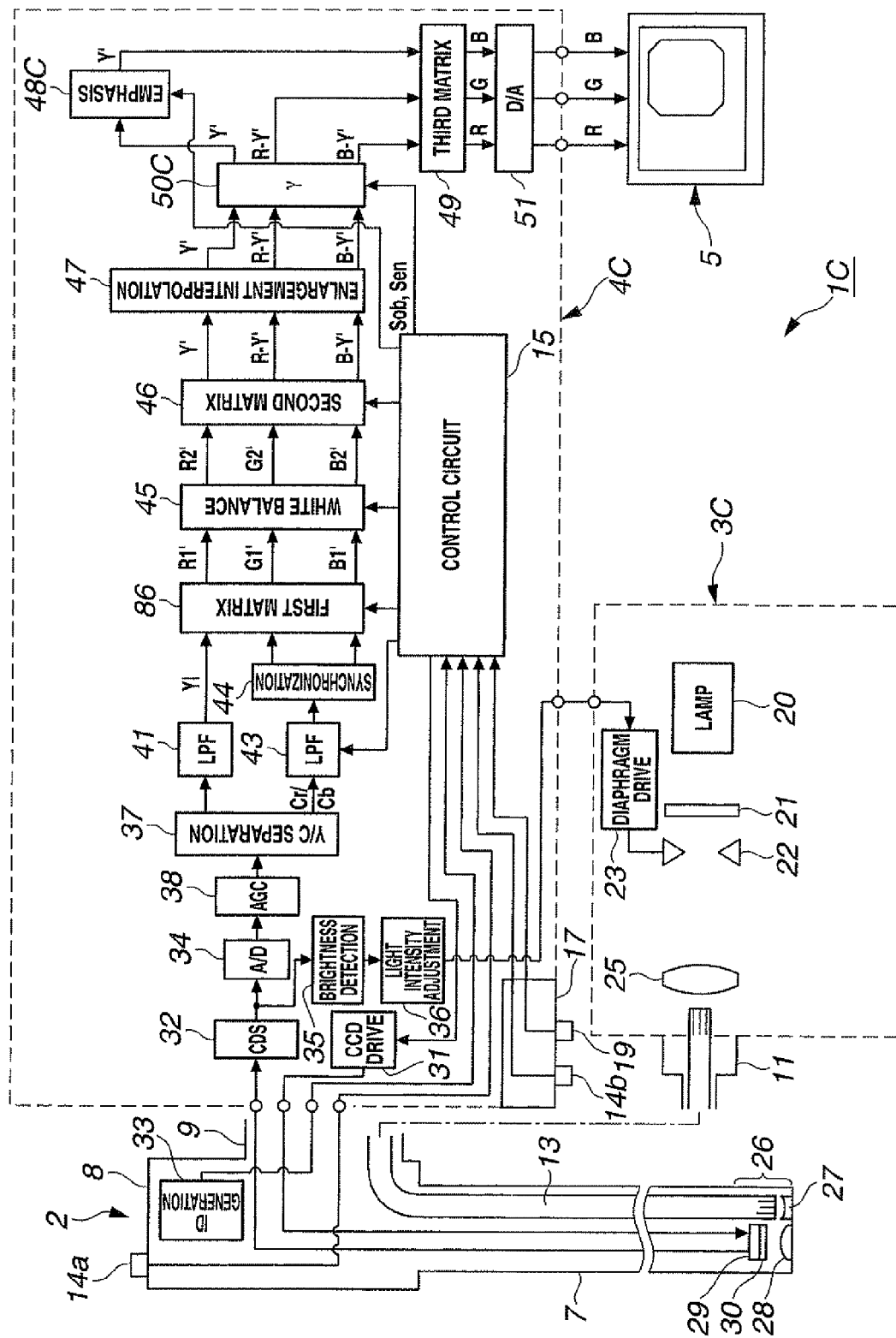
FIG. 11 is a block diagram showing an entire configuration of an endoscope apparatus including embodiment 2 of the present invention.

FIG. 11 shows a configuration of an endoscope apparatus 1C including embodiment 2 corresponding to the case of using the same color separation filter 30 of the complementary color system as the endoscope 2 of embodiment 1.

The endoscope apparatus 1C adopts a light source device 3C with a part of the light source device 3 changed, and a video processor 4C with a part of the video processor 4 changed, in the endoscope apparatus 1 shown in FIG. 1.

The light source device 3C has a configuration which does not have the filter 24 and the filter inserting and ejecting device 16 in the light source device 3 of FIG. 1. Specifically, the light source device 3C always generates white light for ordinary light observation.

Further, in the video processor 4C in the present embodiment, the luminance signal Y1 and the color signals Cr and Cb are input into a first matrix circuit 86 having the function of the first matrix circuit 42 of FIG. 1 through the LPF 41 and LPF 43 and the synchronizing circuit 44 not only in the case of the ordinary light observation mode but also in the case of the narrow band light observation mode, without the selector provided, in the video processor 4 of FIG. 1.

The first matrix circuit 86 converts the luminance signal Y1 and the color signals Cr and Cb into RGB signals (corresponding to R1, G1 and B1 of FIG. 1) at the time of the ordinary light observation mode.

Meanwhile, at the time of the spectral observation mode displaying a spectral image on the display device, the matrix coefficients with three rows and three columns which generate signals of a narrow band (hereinafter, called spectral image signals) are set in the first matrix circuit 86 from the control circuit 15, and the first matrix circuit 86 outputs spectral image signals F1, F2 and F3 of the narrow band.

Therefore, in FIG. 11, the signals which are output from the first matrix circuit 86 are shown by R1', G1' and B1' (here, at the time of the ordinary light observation mode, R1'=R1, G1'=G1, B1'B1; and at the time of the spectral observation mode, R1'=F1, G1'=F2, B1'=F3).

The output signals of the first matrix circuit 86 are made white-balanced signals A2', G2' and B2' by the white balance circuit 45, and are converted into a luminance signal Y', and color difference signals R-Y' and B-Y' by the second matrix circuit 46.

The luminance signal Y' and the color difference signals R-Y' and B-Y' are input into a γ circuit 50C after being subjected to enlargement interpolation processing through the enlargement interpolation circuit 47, and the luminance signal Y' which is tone-converted in the γ circuit 50C is input into an emphasis circuit 48C.

The above described γ circuit 50C has the same configuration as the γ circuit 50 of embodiment 1, for example. Especially for the γ_Edge circuit 55 for emphasizing the contour of an image, the input and output characteristic is switched in accordance with switching of the observation mode and switching of the emphasis level, and processing is performed as in the case of embodiment 1.

In the present embodiment, the input and output characteristic of the γ_Cont circuit may be changed in accordance with the observation mode which is selected.

Thus, the present embodiment adopts the configuration in which from the image pickup signal of the image picked up under illumination of a wide band by white light, an ordinary image signal, and the spectral image signals F1, F2 and F3 corresponding to the image in a narrow band by electric signal processing (numerical date processing) are generated.

When the observation mode is switched in embodiment 1, the illumination light is switched, but switching of the illumination light is not performed in the present embodiment. The control circuit 15 performs switching/setting of the matrix coefficients of the first matrix circuit 86 in accordance with the switching instruction of the observation mode, in other words, switching (selection) of the type of the endoscope image desired to be observed.

In the ordinary light observation mode, processing is performed as in embodiment 1, and in the spectral observation mode, processing is performed as in the case of embodiment 1 by converting the spectral image signals F1, F2 and F3 which are generated by the electric signal processing into the luminance signal Y' and the color difference signals R-Y' and B-Y', whereby noise in the low intensity portion is effectively suppressed.

Further, when switching of the emphasis level by the switching instruction of the emphasis level changeover switch 19 is performed, by switching the input and output characteristic of the γ_Edge circuit 55, processing is performed as in the case of embodiment 1 and noise in the low intensity portion is effectively suppressed, while overshoot at the edge portion in the high intensity portion can be reduced.

Thus, in the present embodiment, noise which is conspicuous in the low intensity can be effectively suppressed as in the case of embodiment 1.

Figure 12:
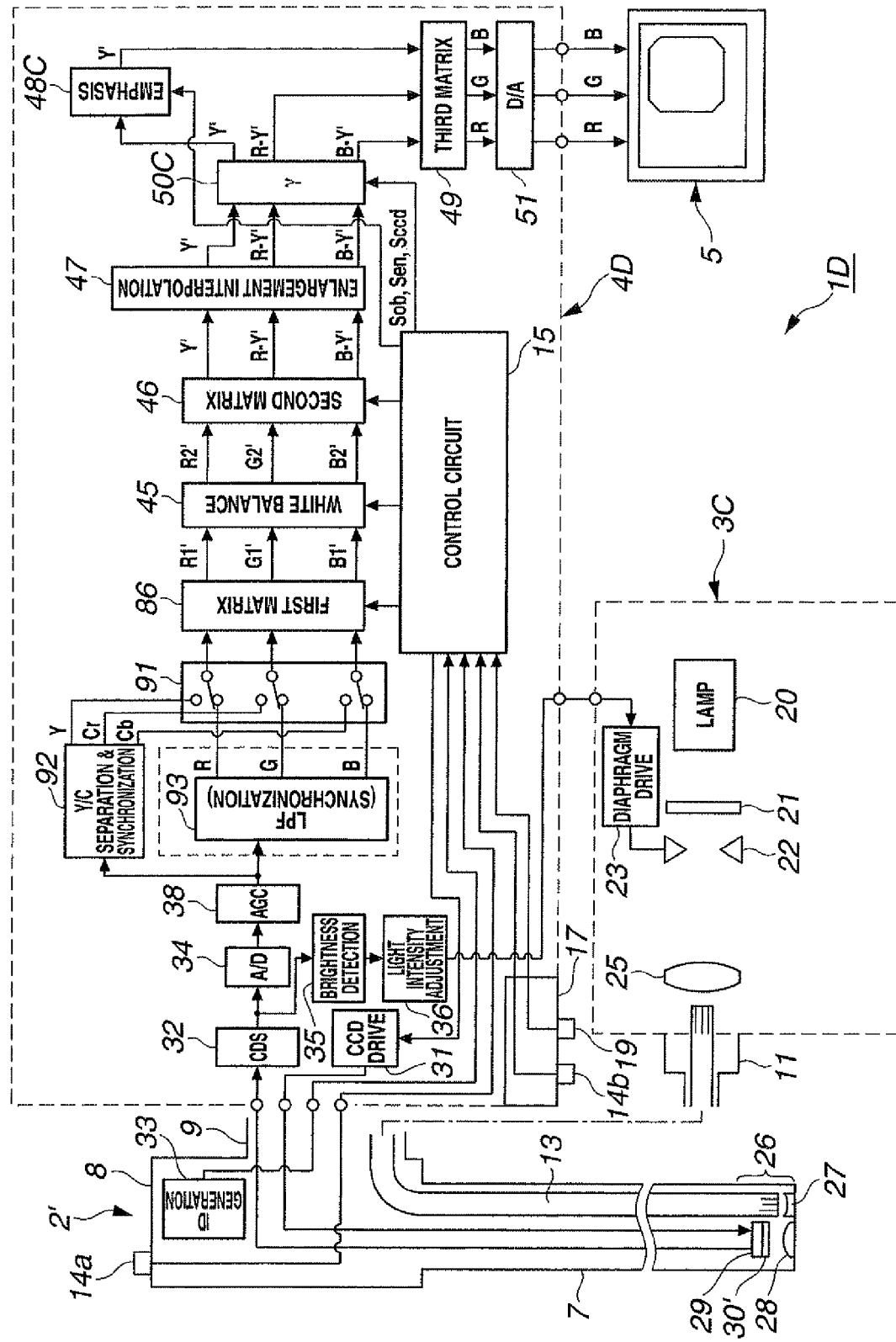
FIG. 12 is a block diagram showing an entire configuration of an endoscope apparatus including a first modified example.

In the above described case, description is made for the endoscope apparatus 1C in the case of the endoscope 2 using the color separation filter 30 of the complementary color system, and a configuration of an endoscope apparatus 1D of a first modified example which can be applied to any case of the endoscope 2 using the color separation filter 30 of the complementary color system and an endoscope 2' using a color separation filter 30' of a primary color system is shown in FIG. 12.

In the endoscope apparatus 1D of FIG. 12, a video processor 4D with a part of the video processor 4C of FIG. 11 changed as follows is used. The video processor 4D is configured to be adaptable to the endoscope 2 including the color separation filter 30 of the complementary color system shown in FIG. 11 and also adaptable to the endoscope 2' using the color separation filter 30' of the primary color system as shown in FIG. 12. The endoscope apparatus 1D shown in FIG. 12 adopts the video processor 4D which is configured to be provided with a changeover switch 91 before the first matrix circuit 86 so as to be able to select a Y/C separating and synchronizing circuit 92 which is applied to the case of the endoscope 2 of the color separation filter 30 of the complementary color system and a synchronizing circuit 93 which is applied to the endoscope 2' using the color separation filter 30' of the primary color system, in the video processor 4C in the endoscope apparatus 1C of FIG. 11.

The Y/C separating & synchronizing circuit 92 in FIG. 12 collectively shows the Y/C separating circuit 37, the LPFs 41 and 43 and the synchronizing circuit 44 in FIG. 11.

The control circuit 15 performs switching of the changeover switch 91, switching/setting of the matrix coefficients of the first matrix circuit 86 and the like based on the information corresponding to the color separation filter 30 or 30' in the ID information from the ID generating section 33 in the endoscope 2 or 2' connected to the video processor 4D.

Further, the control circuit 15 also performs switching control of the characteristic for the emphasis circuit 48C. FIG. 12 shows the case in which the endoscope 2' using the color separation filter 30' of the primary color system is connected to the video processor 4D, and in this case, the synchronizing circuit 93 is selected and used.

The signals of the pixels of R, G and B which are output from the CCD 29 in which the color separation filter 30' of the primary color system is adopted, and are input into the synchronizing circuit 93, are each one color/pixel. Therefore, in the synchronizing circuit 93, they are converted into the signals each of three colors/pixel (three-board) and are output to the first matrix circuit 86.

In the case of the CCD 29 using the color separation filter 30 of the complementary color system, the luminance signal Y and the color signals Cr and Cb are input into the first matrix circuit 86, and in the case of the CCD 29 using the color separation filter 30' of the primary color system, R, G and B signals are input into the first matrix circuit 86.

The control circuit 15 properly performs switching of the matrix coefficients of the first matrix circuit 86 based on the ID information from the ID generating section 33. As described in the case of the configuration of FIG. 11, from the first matrix circuit 86, the signals of R1', G1' and B1' are output.

According to the present modified example, in any case of the case in which the color separation filter 30' of the primary color is used and the case in which the color separation filter 30 of the complementary color system is used, the effect similar to embodiment 2 is obtained.

In the present modified example, based on the ID of the ID generating section 33, the characteristic of; for example, the γ_Edge circuit 55 in the γ circuit 50C may be properly set in accordance with the characteristic of the CCD 29 equipped in the endoscope 2 or 2'.

Specifically, since the value of S/N at the time of photoelectric conversion differs in accordance with the type of the CCD or the like, the γ_table value of the characteristic corresponding to the value of the S/N is stored in the γ_table storing section 56 (see FIG. 4) in the γ circuit 50C, in accordance with the type or the like of the CCD 29.

Subsequently, the control circuit 15 sends an instruction signal Sccd using the γ_table value corresponding to the CCD 29 from the ID of the ID generating section 33 to the γ_table storing section 56 in the γ circuit 50C, and the γ_table storing section 56 sets the instructed γ_table value in the γ_Edge circuit 55.

The instruction signal Sccd causes a suitable one of the γ_table values to be set in correspondence with the type or the like of the CCD which is actually used, in addition to having the function of causing the γ_table value to be set in the γ_Edge circuit 55 based on switching of the emphasis level and the observation mode.

In this case, in the case of the CCD 29 with small S/N, the CCD 29 is set at such a characteristic that the output value becomes a low value with respect to the input of the low intensity portion as compared with the case of the CCD 29 with large S/N. By doing so, even when the characteristic of the CCD 29 differs, noise especially in the low intensity portion can be effectively suppressed.

The γ table value which is set in the γ_Edge circuit 55 may be set based on the instruction signal Sccd, the instruction signal Sen corresponding to the emphasis level, and the instruction signal Sob corresponding to the observation mode.

Figure 13:
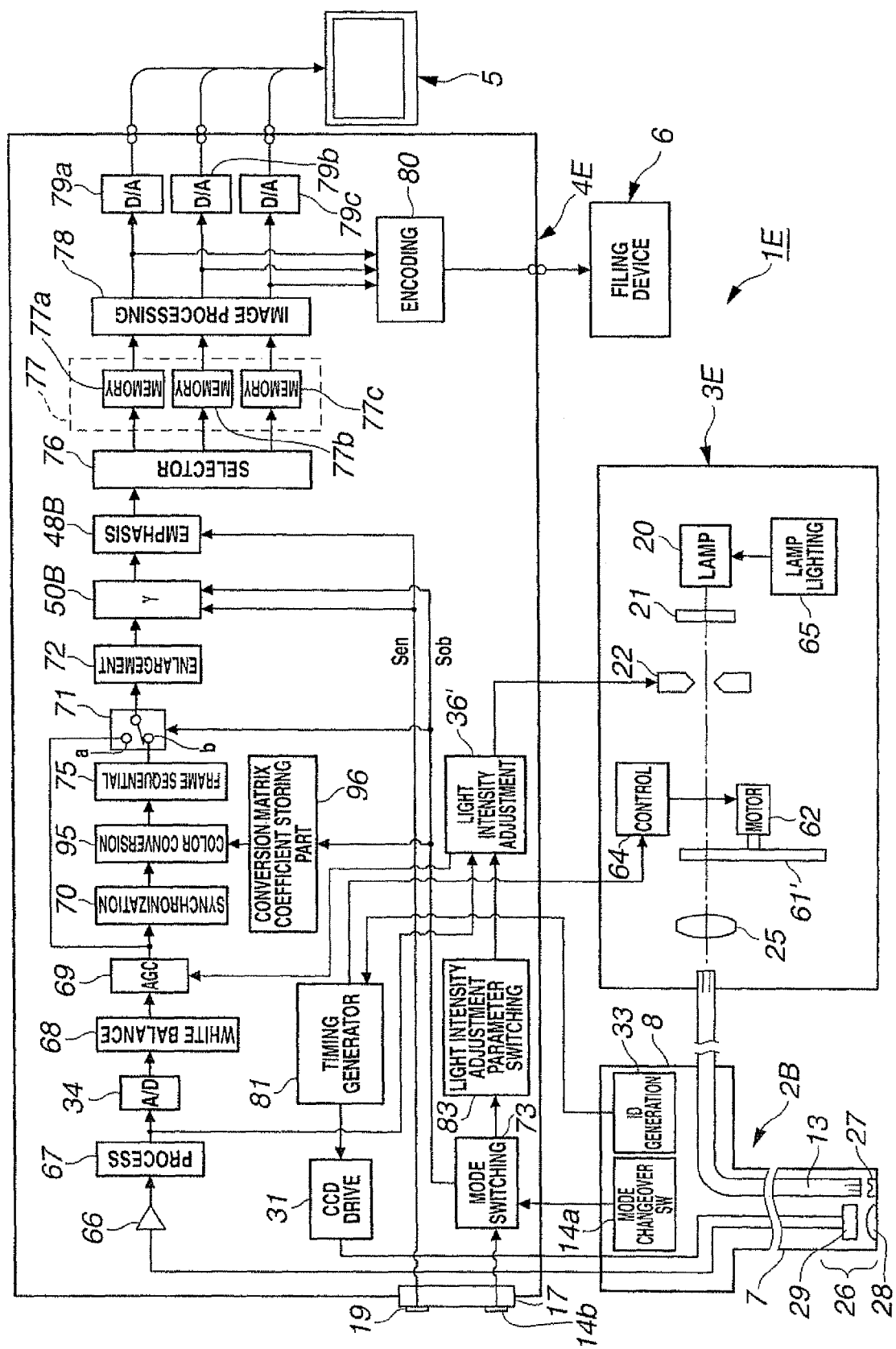
FIG. 13 is a block diagram showing an entire configuration of an endoscope apparatus including a second modified example.

The present embodiment can be also applied to the case of the frame sequential type endoscope 2B. FIG. 13 shows an endoscope apparatus 1E including the second modified example applied to the case of the frame sequential type endoscope 2B.

The endoscope apparatus 1E adopts a light source device 3E with a part of the light source device 3B changed, and a video processor 4E with a part of the video processor 4B changed, in the endoscope apparatus 1B shown in FIG. 7.

The light source device 3E is configured so that a rotary filter 61' is used instead of the rotary filter 61, and the moving motor 63 and the like which move the rotary filter 61 are not provided, in the light source device 3B of FIG. 7.

Specifically, the rotary filter 61' has only the filter group at the outer circumferential side shown in FIG. 8, and does not have the filter group at the inner circumferential side. The rotary filter 61' always generates frame sequential light of R, G and B.

Further, the video processor 4E has a color converting circuit 95 which includes the function of generating a spectral image signal of a narrow band and the function of performing color conversion for the generated spectral image signal (corresponding to the function of the color converting circuit 74 of FIG. 7), instead of the color converting circuit 74, in the video processor 4B of FIG. 7.

Further, a conversion matrix coefficient storing section 96 which supplies the conversion matrix coefficients for generating a spectral signal of a narrow band to the color converting circuit 95 is provided. When mode switching to the spectral light observation mode is performed, the conversion matrix coefficients for generating a spectral signal of a narrow band are supplied to the color converting circuit 95 from the conversion matrix coefficient storing section 96 by the signal from the mode switching circuit 73.

The spectral image signal is generated and color conversion is performed by the color converting circuit 95, and the signal corresponding to the narrow band signal output from the color converting circuit 74 of FIG. 7 is output to the frame sequential circuit 75. The other configuration is the same as that of FIG. 7.

Further, at the time of the ordinary light observation mode, the operation by the present modified example is totally the same operation of the ordinary light observation mode in the case of FIG. 7.

On the other hand, at the time of the spectral light observation mode, the conversion matrix coefficients are supplied to the color converting circuit 95 from the conversion matrix coefficient storing section 96, a spectral image signal is generated, and color conversion is further performed. The color-converted spectral image signal which is output from the color converting circuit 95 corresponds to the light-converted narrow band signal which is output from the color converting circuit 74 of FIG. 7. The operation from the color converting circuit 95 and thereafter is the same operation as that of the spectral observation mode of FIG. 7.

The present modified example can be also applied to the case of generating an image signal of a narrow band, that is, a spectral image signal from an image signal of a broad band of a frame sequential type in the ordinary light observation mode, and noise in the low intensity portion in that case can be effectively suppressed.

In the above described embodiment 2 and modified example of it, the case of the spectral observation mode is described as the special light observation mode.

Further, as the special light observation mode, the present invention can be applied to the cases of an infrared light observation mode in which infrared light is irradiated to a specimen such as an affected part, and a fluorescent observation mode in which fluorescent observation is performed by irradiating excitation light, instead of the narrow band light observation mode described in embodiment 1, for example.

For example, in the case of the infrared light observation mode, or the fluorescent observation mode, illumination light of at least one narrow band is irradiated, and an infrared light image or a fluorescent image can be obtained from an image signal picked up under the illumination light, as in the case of the narrow band light observation mode described in embodiment 1.

Further, embodiments and the like which are configured by the above described respective embodiments and the like being partially combined and the like also belong to the present invention.

What is claimed is:

1. An image processing device for an endoscope, comprising:
    an image processing section which performs signal processing for generating an image signal which is to be observed as an endoscope image and corresponds to the endoscope image, for a signal picked up with an image pickup device equipped in the endoscope;
    a tone correcting circuit section which corrects a tone for the image signal; and
    a switching section which switches an observation mode or a type for observing as an endoscope image;
    wherein the switching section is capable of switching to optional one from endoscope images including at least two observation modes or types out of an ordinary light image generated under illumination light of a visible wavelength region, a special light image generated under illumination light differing from the ordinary light image, and a spectral image corresponding to a narrow band image generated by applying numerical data processing to the image signal generated under the illumination light of the visible wavelength region;
    wherein the tone correcting circuit section includes: a first tone correcting circuit section which corrects the tone of the image signal with a first correction characteristic; and a second tone correcting circuit section which has a second correction characteristic differing from the first correcting circuit section, and corrects a tone for an input image signal which is input into an emphasis circuit section which performs emphasis of sharpness for the image signal;
    wherein the second tone correcting circuit section changes the second correction characteristic for intensity in the input image signal, in correspondence with switching of the observation mode or the type, or switching of the emphasis amount; and
    wherein the second tone correcting circuit section further changes to the second correction characteristic having such an input and output characteristic as to provide an output value smaller in a case in which the endoscope image is the special light image or the spectral image than in a case of the ordinary light image.

2. The image processing device for an endoscope according to claim 1, further comprising the emphasis circuit section which performs emphasis of sharpness for the image signal, and an emphasis amount switching section which performs switching of an emphasis amount of the sharpness.

3. The image processing device for an endoscope according to claim 2, wherein the tone correcting circuit section changes the correction characteristic of the tone in correspondence with an emphasis amount set by switching of the emphasis amount.

4. The image processing device for an endoscope according to claim 1,
    wherein the second tone correcting circuit section changes the second correction characteristic in correspondence with switching of the observation mode or the type, or switching of the emphasis amount.

5. The image processing device for an endoscope according to claim 4,
    wherein the second tone correcting circuit section has a data storing section storing data for determining the second correction characteristic, and changes the data in accordance with switching of the observation mode or the type, or the emphasis amount.

6. The image processing device for an endoscope according to claim 1,
    wherein the tone correcting circuit section changes the correction characteristic of the tone to correction characteristics differing from each other at least in a case of switching to the ordinary light image, and a case of switching to the special light image or the spectral image.

7. The image processing device for an endoscope according to claim 1,
wherein the second tone correcting circuit section changes to the second correction characteristic having such an input and output characteristic as to provide an output value smaller in a case of switching for making the emphasis amount large than in a case of switching for making the emphasis amount small.

8. The image processing device for an endoscope according to claim 1,
wherein the special light image is any of a narrow band light image generated from an image signal picked up under at least one narrow band illumination light, a fluorescent image and an infrared light image.

9. The image processing device for an endoscope according to claim 1, wherein the special light image is a narrow band image generated by the image processing section based on a signal picked up with the image pickup device under illumination light of a narrow band wavelength region.

10. The image processing device for an endoscope according to claim 1, wherein the second tone correcting circuit section has a data storing section storing data for determining the second correction characteristic, and in a case in which the endoscope image is the special light image or the spectral image, the second tone correcting circuit section reads corresponding data out from the data storing section and changes to the second correction characteristic having such an input and output characteristic as to provide an output value smaller than in a case of the ordinary light image.

11. An image processing device for an endoscope, comprising:
an image processing section which performs signal processing for generating an image signal which is to be observed as an endoscope image and corresponds to the endoscope image, for a signal picked up with an image pickup device equipped in an endoscope;
a tone correcting circuit section which corrects a tone for the image signal;
an emphasis circuit section which performs emphasis of sharpness for the image signal;
a switching section which switches an observation mode or a type for observing as an endoscope image; and
an emphasis amount switching section which performs switching of an emphasis amount of the sharpness;
wherein the switching section is capable of switching to optional one from endoscope images including at least two of an ordinary light image generated under illumination light of a visible wavelength region, a special light image generated under illumination light differing from the ordinary light image, and a spectral image corresponding to a narrow band image generated by applying numerical data processing to the image signal generated under the illumination light of the visible wavelength region;
wherein the tone correcting circuit section includes: a first tone correcting circuit section which corrects the tone of the image signal with a first correction characteristic; and a second tone correcting circuit section which has a second correction characteristic differing from the first correcting circuit section, and performs correction of a tone for an input image signal which is input into the emphasis circuit section;
wherein the second tone correcting circuit section changes the second correction characteristic for low intensity in the input image signal, in correspondence with switching of the observation mode or the type, or switching of the emphasis amount; and
wherein the second tone correcting circuit section further changes to the second correction characteristic having such an input and output characteristic as to provide an output value smaller in a case in which the endoscope image is the special light image or the spectral image than in a case of the ordinary light image.

12. The image processing device for an endoscope according to claim 11,
wherein the second tone correcting circuit section changes the second correction characteristic in correspondence with switching of the observation mode or the type, or switching of the emphasis amount.

13. The image processing device for an endoscope according to claim 11,
wherein a correction characteristic by the tone correcting circuit section is changed to correction characteristics differing from each other at least in a case of switching to the ordinary light image, and a case of switching to the special light image or the spectral image.

14. The image processing device for an endoscope according to claim 11, wherein the second tone correcting circuit section changes to the second correction characteristic having such an input and output characteristic as to provide an output value smaller in a case of switching for making the emphasis amount large than in a case of switching for making the emphasis amount small.

15. The image processing device for an endoscope according to claim 11,
wherein the special light image includes any of a narrow band light image generated from an image signal picked up under irradiation of at least one narrow band illumination light, a fluorescent image and an infrared light image.

16. The image processing device for an endoscope according to claim 11,
wherein the second tone correcting circuit section has a data storing section storing data for determining the second correction characteristic, and changes the data in accordance with switching of the observation mode or the type, or the emphasis amount.

17. The image processing device for an endoscope according to claim 11, further comprising an output characteristic changing circuit configured to change, in a case in which the emphasis circuit section performs emphasis at a small emphasis level, an output characteristic of the emphasis circuit section such that the output characteristic has a smaller output value on a low luminance side than an output characteristic of the tone correcting circuit section, in accordance with switching of the observation mode or the type, or switching of the emphasis amount.

18. The image processing device for an endoscope according to claim 11, further comprising an output characteristic changing circuit configured to change, in a case in which the emphasis circuit section performs emphasis at a large emphasis level, an output characteristic of the emphasis circuit section such that the output characteristic has a smaller output value over an entire luminance region than an output characteristic of the tone correcting circuit section, in accordance with switching of the observation mode or the type, or switching of the emphasis amount.

19. The image processing device for an endoscope according to claim 11, wherein the special light image is a narrow band image generated by the image processing section based on a signal picked up with the image pickup device under illumination light of a narrow band wavelength region.

* * * * *